United States Patent [19]

Kittleson et al.

[11] Patent Number: 5,437,991
[45] Date of Patent: Aug. 1, 1995

[54] PROCESS FOR THE SYNTHESIS NATURAL AROMATICS

[75] Inventors: Jeanine R. Kittleson, Villa Park; David P. Pantaleone, Buffalo Grove, both of Ill.

[73] Assignee: The NutraSweet Company, Deerfield, Ill.

[21] Appl. No.: 236,612

[22] Filed: May 2, 1994

[51] Int. Cl.$^6$ .......................... C12P 13/00; C12P 7/62
[52] U.S. Cl. ................................... 435/128; 435/135; 435/198; 435/921
[58] Field of Search ................ 435/135, 128, 198, 921

[56] References Cited

U.S. PATENT DOCUMENTS

| 5,200,330 | 4/1993 | Page et al. | 435/135 |
| 5,219,733 | 6/1993 | Myojo et al. | 435/135 |

FOREIGN PATENT DOCUMENTS

| 2588272 | 4/1987 | France | 435/135 |
| 2107791 | 5/1987 | Japan | 435/135 |
| 3219897 | 9/1991 | Japan | 435/135 |
| 4003623 | 2/1994 | WIPO | 435/135 |

OTHER PUBLICATIONS

Miller et al "JAOCS" vol. 65 No. (Jun. 1985) pp. 927–931.
Chen et al "J. Am. Chem. Soc." vol. 109 No. 9 (1987) pp. 2812–2817.
Lazar et al "World Conference of Emerging Tech" Fats, Oils, Ind (1985) pp. 346–354.
Derwent ABS (J52070057) Jun. 1977 Ohoshi Syoyu.
Derwent ABS J51061673 (May 1976) Snow Brand Milk.

Primary Examiner—Herbert J. Lilling
Attorney, Agent, or Firm—Paul & Paul

[57] ABSTRACT

A novel method for the production of natural aromatic ester compounds such as methyl anthranilate, ethyl anthranilate butyl anthranilate methyl cinnamate and methyl salicylate comprises the esterification of their corresponding acids using microbially derived enzymes in the presence of a $C_1$–$C_4$ alcohol such as methanol, ethanol or butanol. A biphasic reaction medium may optionally be utilized to generate maximum yields through the addition of a non-polar organic solvent such as hexane, ethyl acetate, heptane and the like.

13 Claims, 2 Drawing Sheets

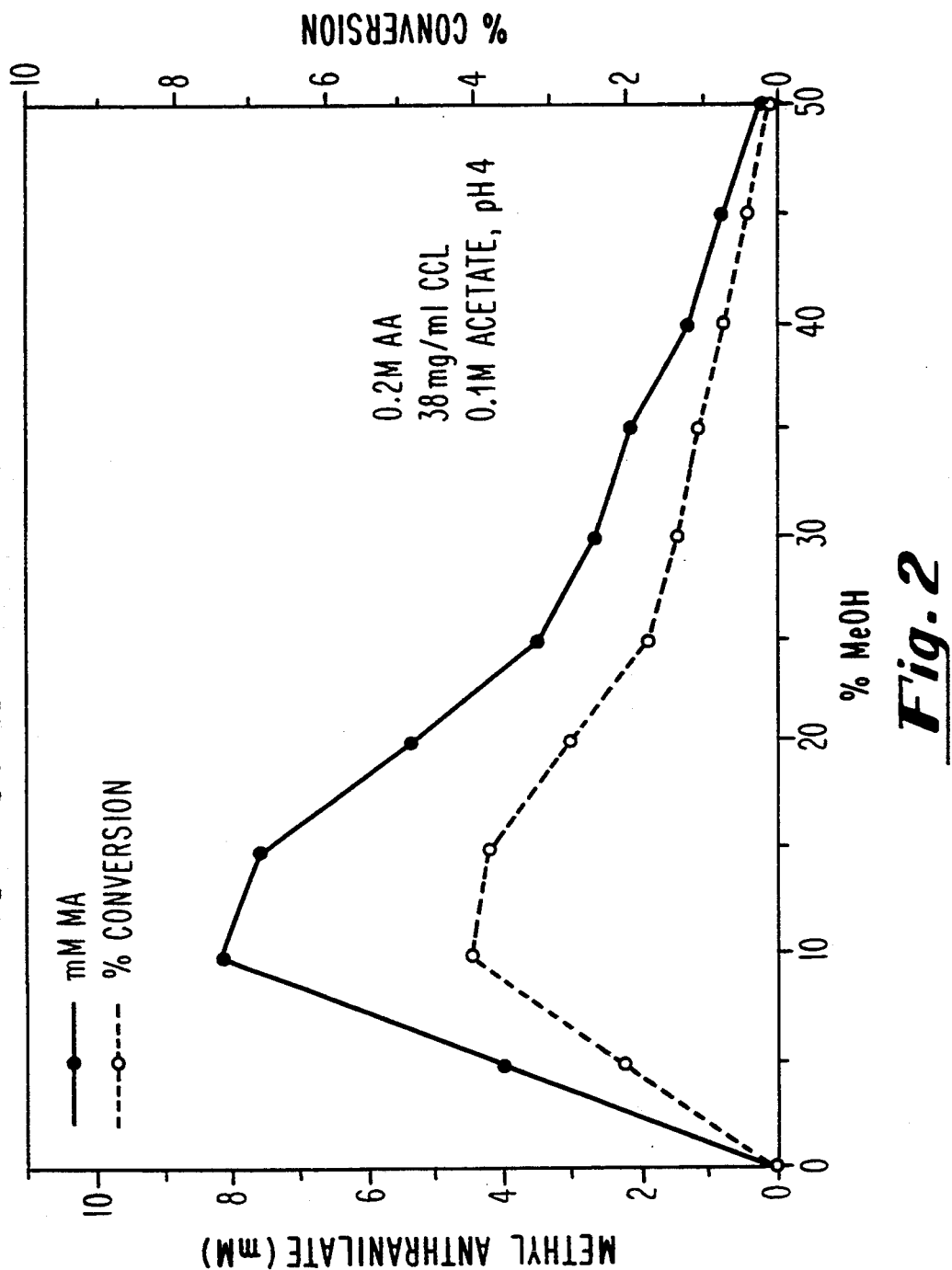

PROCESS FOR THE SYNTHESIS NATURAL AROMATICS

BACKGROUND OF THE INVENTION

The present invention relates generally to the synthesis of aromatic compounds and in particular, those compounds that possess fresh, fruity characteristics and notes. In recent years there have been a strong consumer demand for things that are natural, and this preference is nowhere more prevalent than the choice of natural flavors over synthetic substitutes. In order to successfully fulfill this demand, new methods are required for producing those compounds responsible for these natural aromas and notes.

Grape flavors are always in demand as a flavor component in foodstuffs and beverages and concord grape, in particular, has a unique and pleasant taste and aroma. Methyl anthranilate for example, is known to be major contributor to the aroma of this fruit and is in fact regarded as an impact compound as an essential component for its flavor. It is also often used as an indispensable ingredient in other flavoring systems. This ester is often used industrially in different food flavorings and perfume compositions. Described as a "green apple odor" it has also been identified in several essential oils such as neroli, bergamot and wood strawberry. Although it is widely distributed in nature, it is not readily extracted and economically feasible to isolate due to its low levels when present in a particular source. Ethyl anthranilate is a derivative responsible for peach, berry, grape and orange flavors while butyl anthranilate is an important aromatic in plum flavors and perfumes. Other valuable aromatic ester flavor compounds include methyl salicylate and methyl cinnamate.

Two known methods for the production of natural methyl anthranilate include the bioconversion (demethylation) of dimethyl anthranilate (N-methyl methyl anthranilate) to methyl anthranilate by Trametes and Polyporous fungi and the fermentation thereof by another fungal group *Pyconoporous Cinnabarinus*. Since the starting material needed in the demethylation reaction of the first process is in limited supply and is actually quite scarce, and the fermentation process only yields very low titres, the cost of natural methyl anthranilate is fairly high.

U.S. Pat. No. 5,200,330 to Page et. al. discloses microbially mediated N-demethylation of dimethyl anthranilate to yield methyl anthranilate using cultures of *Trametes versicolor* and *Polyporous sovalis*, two species of fungi. However, not only are the yields of methyl anthranilate low, but a secondary byproduct, N-formylmethyl anthranilate is also produced. Another problem that exists in attempts to microbially ferment methyl anthranilate through the demethylation of dimethyl anthranilate is that both the starting material and the product are highly toxic to most microorganisms. Moreover, the substrate stereochemistry is problematical because the microbiological demethylations are enzymatic and hence are highly selective.

Gross et. al., *App. Microbi. and Biotech.* (1990) 34-387-391 reports the synthesis of methyl anthranilate from *Pycnoporous cinnabarinus* fermentation from a culture medium containing diammonium tartrate, sugars and maltose. Again unfortunately, relatively low yield levels are obtained.

Another possible route is the esterification of anthranilic acid. Chemical esterification involves the reaction of anthranilic acid in methanol with an acid catalyst at high temperatures. This is not considered a natural procedure however, and must be run at high temperatures which is not suitable for many applications. U.S. Pat. No. 3,189,529 to Yamado et. al. discloses a method for the isolation and purification of a high activity lipase from a culture of the yeast *Candida cylindraea*. Gillies et. al., *Biocatalysis in Organic Medium* 227 (1986) reported on the production of natural flavor esters such as ethyl butyrate and isoamyl butyrate using this same lipase absorbed onto silica gel.

The present invention provides a means to overcome the problems of low yields while still utilizing a natural process. The present invention more specifically relates to the use of enzymes to esterify natural anthranilic acid, cinnamic acid and salicylic acid to form natural methyl anthranilate, methyl cinnamate and methyl salicylate, respectively. The enzymes found to be of use are able to catalyze the esterification reaction at moderate temperatures which makes it easier to run and is suitable for all applications. And of course, the added benefit remains that the chemicals consumed in the process as well as the methyl anthranilate final product may all be classified as natural.

SUMMARY OF THE INVENTION

A novel method for the synthesis of natural aromatic ester flavor compounds comprises the enzymatic esterification of its corresponding acid in the presence of methanol to yield methyl anthranilate, methyl cinnamate, and methyl salicylate, respectively. Ethanol and butanol can be used in place of methanol to yield the ethyl and butyl derivatives, respectively. These compounds are responsible for grape, cinnamon, orange, peach and wintergreen aromas and are highly prized additives yet are relatively rare in nature.

BRIEF DESCRIPTION OF THE DRAWINGS

FIG. 2 is a line graph plotting methyl anthranilate production as a function of methanol concentration.

FIG. 3 is a line graph plotting anthranilate production as a function of hexane concentration.

DETAILED DESCRIPTION OF THE INVENTION

Figure 1:
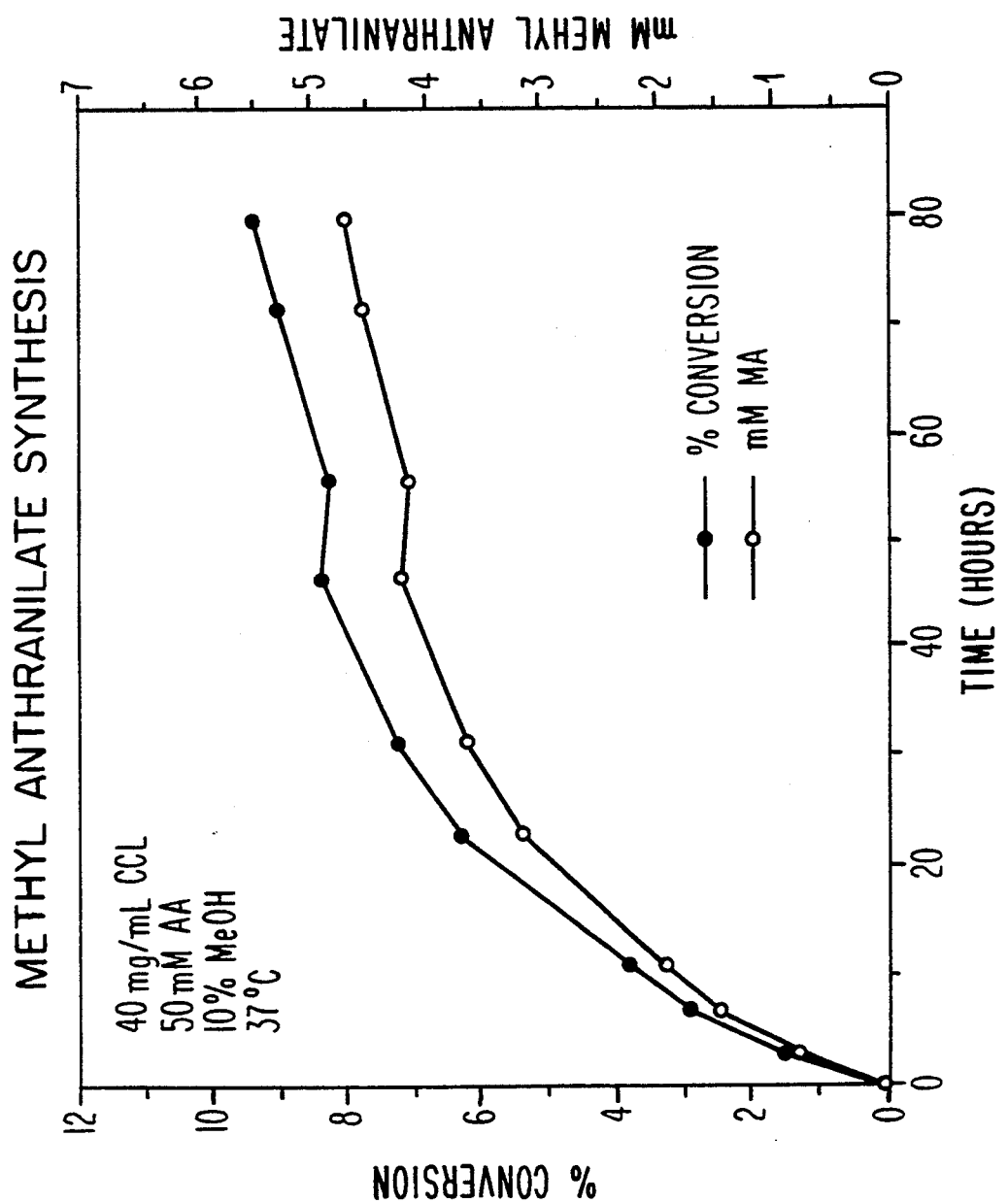
FIG. 1 is a line graph plotting the rate of methyl anthranilate production as a function of time.

The present invention utilizes naturally derived enzymes to esterify natural acids to produce flavor compounds such as methyl anthranilate, methyl cinnamate and methyl salicylate. In essence, the aromatic flavor compound is the methyl ester of its corresponding acid. Anthranilic acid, for example is used in the general reaction:

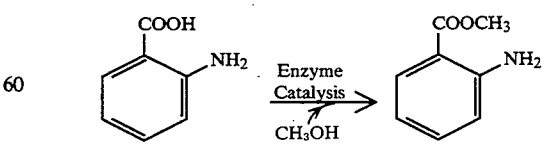

which when esterified in the presence of the appropriate enzyme and reaction medium yields methyl anthranilate as shown.

Methyl cinnamate may also be naturally synthesized as follows:

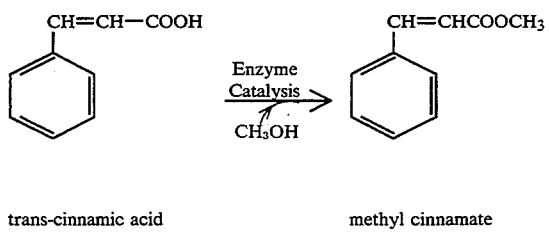

trans-cinnamic acid   methyl cinnamate

And Methyl salicylate, an important component of wintergreen oil, may be naturally derived using the same microbially derived lipase

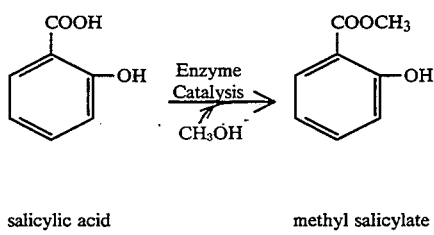

salicylic acid   methyl salicylate

Ethyl anthranilate and butyl anthranilate may also be produced according to the method of the present invention. The acid is esterified using the same lipase under the same reactionary conditions with the exception that the $C_1$–$C_4$ alcohol that comprises a secondary substrate in the reaction mixture is not methanol but rather ethanol or butanol, respectively. While not the impact aromatic compound that methyl anthranilate is, these compounds possess their own distinctive aromatic characteristics that are useful in food and beverage applications. Ethyl anthranilate is for example, useful as an aromatic essence in berry, grape, orange and peach flavors while butyl anthranilate provides plum flavor and is a valuable essence in perfumes.

It was discovered that the three components of the reaction mixture, the enzyme, the acid and the $C_1$–$C_4$ alcohol are not only involved in the synthesis per se but also interact with each other. Other parameters such as solvent, pH, temperature, reaction time and agitation also affect production. It was initially realized for example, that in order for anthranilic acid to react with methanol to form methyl anthranilate, the acid must be solubilized and the carboxyl group protonated. The reaction must take place at a pH low enough so that the anthranilic acid is protonated but not so low that the enzymes catalytic abilities are reduced. Anthranilic acid is also very soluble in methanol so the greater the methanol concentration, the greater the solubility of the substrate.

Proteases, esterases and lipases may be used to carry out this synthetic reaction. Preferably, a commercial lipase obtained from *Candida cylindracae* is used to catalyze the reaction. *C. cylindracae*, also termed *C. rugosa* is a yeast fermented to yield a lipolytic enzyme preparation commercially available, for example from the Amano Int'l Enzyme Co., Troy, Va. The enzyme catalyzes the reaction between the two substrates, methanol and anthranilic acid in an aqueous solution with a methanol concentration of from approximately 5% to about 50% w/v and preferably from about 5% to about 30%. The methanol provides the methyl group for the esterification of the acid. A small amount of an acetate buffer is added to acidify the pH of the system to a range of from about 2.0–5.0. The reaction is run at moderate temperature of from approximately 30° C. to about 50° C. and may run from 2–100 hours, generally from about 10–15 hours.

Optionally, a secondary non-polar organic solvent may be added to the aqueous solution to provide a biphasic reaction medium. Suitable non-polar solvents include hexane, ethyl acetate, heptane, isopropyl ether, methoxy ethyl ether, petroleum ether, glycerol, butyl ether, t-butyl methyl ether, and mixtures thereof. Preferably, hexane or ethyl acetate are the solvents of choice. The addition of this non-polar solvent significantly increases the methyl anthranilate yield. It is believed that the solvent such as hexane solubilizes the methyl ester product thereby "removing" it from the aqueous phase which contains the enzyme and shifts the reaction's equilibrium towards product formation. Because the enzyme's rate of catalysis is not inhibited by high concentrations of product as it is produced, the enzyme drives the reaction further than it otherwise would have. The hexane may be added in an amount of from about one (1) to three (3) times the amount of the of the aqueous system and this results in yields of up to about 1 to 4 times the yield produced when no hexane is added.

The following examples are provided to more fully set forth and describe that which comprises the present invention. They are for illustrative purposes only however, and it is realized that minor changes and alterations can be made which ar not specifically disclosed therein. Such modifications that do not materially alter the invention are intended to be included herein, as falling within the spirit and scope of the invention defined by the claims that follow.

EXAMPLE 1

100 mg. of *Candida Cylindracea* lipase (CCL) was solubilized in 1.6 mL acetate buffer, pH 5.0. To this solution was added 0.4 mL of 1M anthranilic acid in methanol for a final concentration of 0.2M anthranilic acid, 20% methanol, respectively, and a final pH of 4.0. The reaction was incubated at 37° C. at an agitation rate of 300 rpm for 72 hours. HPLC analysis of the reaction solution indicated 5.4% of the anthranilic acid had been converted to methyl anthranilate by CCL lipase. The identity of this compound was confirmed as methyl anthranilate by TLC, HPLC and 'H—NMR.

EXAMPLE 2

The procedure set forth in Example 1 was repeated using the following amounts of reaction components

| | |
|---|---|
| CCL lipase | 40 mg/ml |
| Anthranilic Acid | 50 mM |
| Methanol | 10% |
| Temperature | 37° C. |

Referring now to FIG. 1, the amount of product, methyl anthranilate is plotted as a function of time. As is clearly shown, the equilibrium reaction begins to slow down after 30–40 hours but production continues nevertheless to 80 hours and beyond. Hence, higher yields can be realized with increasing reaction times.

EXAMPLE 3

The procedure set forth in Example 1 was repeated using the same reactants in the following amounts.

| | |
|---|---|
| Anthranilic Acid | 0.2M |
| CCL lipase | 38 mg/ml |
| Acetate | 0.1 m; pH 4 |

Referring now to FIG. 2, the amount of methyl anthranilate production is plotted as function of methanol concentration. It becomes readily evident that the rate of reaction slows considerably after the concentration reaches a level of just over 10%. The methanol concentration has this effect because alcohols tend to denature proteins which enzymes are of one type. Their denaturation consequently reduces their catalytic activity and the presence of methanol then, as a substrate, eventually inhibits enzyme activity and anthranilate production. It also bears out that a methanol concentration of approximately 10% is optional.

EXAMPLE 4

The reaction synthesis of example 1 was again repeated using the following components in the amounts/concentrations listed.

| | |
|---|---|
| Anthranilic Acid | 0.1M |
| Methanol | 10% |
| CCL lipase | 40 mg/ml |
| Acetate | 20 mM |

The reaction was run at a pH of 4.0 at 37° C. for approximately 5 days (120 hours). Referring now to FIG. 3, methyl anthranilate production is plotted as a function hexane concentration. As can be seen therein, addition of hexane in amounts of approximately 20%–50% significantly increases methyl anthranilate production, but levels above 60% cause production rates to drastically fall off. This would indicate that the presence of hexane at high concentrations, like methanol, tends to inhibit enzyme activity by denaturation of the enzyme protein.

At lower levels however, hexane (and other water immiscible solvents) pushes the reaction toward completion (product formation) by solubilizing the methyl anthranilate product (which is not very water soluble but is soluble in alcohols and other organic solvents) and therefore reduces the products' concentration in the aqueous phase where the enzyme is. The reduced concentration of methyl anthranilate in the aqueous phase then pushes the reaction to the right toward more methyl anthranilate formation.

What we claim is:

1. A method for the preparation of natural aromatic ester flavor compounds selected from the group consisting of methyl anthranilate, ethyl anthranilate, butyl anthranilate, methyl cinnamate and methyl salicylate from their corresponding acids comprising mixing said acid with a $C_1$–$C_4$ alcohol in an aqueous or biphasic reaction medium and catalyzing an esterification reaction with a lipase derived from the microorganism Candidia cylindracea.

2. The method of claim 1 wherein said acid is selected from the group consisting of anthranilic acid, salicylic acid, cinnamic acid and mixtures thereof.

3. The method of claim 2 wherein said $C_1$–$C_4$ alcohol is selected from the group consisting of methanol, ethanol, butanol and mixtures thereof.

4. The method of claim 3 wherein the concentration of the $C_1$–$C_4$ alcohol is from approximately 2.0% to about 50%.

5. The method of claim 4 wherein said alcohol concentration is from about 5% to about 30%.

6. The method of claim 5 wherein the pH of said esterification reaction is maintained at about 4.8.

7. The method of claim 6 where said esterification is carried out in a biphasic reaction medium.

8. The method of claim 7 where said biphasic reaction medium is brought about through the addition of a secondary non-polar organic solvent.

9. The method of claim 8 wherein said non-polar hexane organic solvent which is added in an amount of about 0% to about 30% w/v.

10. The method of claim 9 wherein said non-polar solvent is selected from the group consisting of hexane, ethyl acetate, heptane, isopropyl ether, methoxy ethyl ether, petroleum ether, glycerol, butyl ether, t-butyl methyl ether and mixtures thereof.

11. The method of claim 10 wherein said non-polar solvent is selected from the group consisting of hexane, ethyl acetate and mixtures thereof.

12. The method of claim 10 wherein said non-polar solvent is to said reaction mixture in a ratio of from about 1:1 to about 1:5 w/v, respectively.

13. The method of claim 12 wherein said hexane is added to said reaction mixture in a ratio of about 1:3 w/v respectively.

* * * * *